United States Patent [19]

Gansow

[11] Patent Number: 4,824,986

[45] Date of Patent: Apr. 25, 1989

[54] METAL CHELATE PROTEIN CONJUGATE

[75] Inventor: Otto Gansow, Washington, D.C.

[73] Assignee: The United States of America as represented by the Secretary of the Department of Health and Human Services, Washington, D.C.

[21] Appl. No.: 727,919

[22] Filed: Apr. 26, 1985

[51] Int. Cl.$^4$ .................... C07C 161/04; C07C 79/40; C07D 207/40

[52] U.S. Cl. ..................................... 558/17; 548/547; 562/553

[58] Field of Search .......................... 548/547; 558/17; 562/553

[56] References Cited

U.S. PATENT DOCUMENTS 4,454,106 6/1984 Gansow et al. ........................ 558/17
4,472,509 9/1984 Gansow et al. ........................ 558/17

FOREIGN PATENT DOCUMENTS 2109407 6/1983 United Kingdom ................ 558/17

OTHER PUBLICATIONS

Chemical Abstracts, vol. 83, No. 8, 1975, Sundberg et al., "Chelating Agents for the Binding of Metal Ions to Macromolecules", 587-8.
Biological Abstract, vol. 80, No. 3, 1985, Lauffer et al., "Preparation and Water Relaxation Properties of Proteins Labeled with Paramagnetic Metal Chelates", 11-16.
International PCT Search Report.
Yeh et al, "A New Route to 'Bifunctional' Chelating Agents: Conversion of Amino Acids to Analogs of Ethylenedinitrilotetraacetic Acid," Analytical Biochemistry, 100, 152-159 (1979).
Meares et al, "Metal Chelates as Probes of Biological Systems," Acc. Chem. Res., 17, 202-209 (1984).

Primary Examiner—Mary C. Lee
Assistant Examiner—Robert C. Whittenbaugh
Attorney, Agent, or Firm—Holman & Stern

[57] ABSTRACT

A method of forming a novel metal chelate protein conjugate is described. Also described are metal chelates and precursor compounds to the metal chelates. The novel metal chelate protein conjugates are particularly useful in the diagnostic imaging of tumors and in tumor therapy.

2 Claims, No Drawings

METAL CHELATE PROTEIN CONJUGATE

BACKGROUND OF THE INVENTION

This invention relates to metal chelate protein conjugates and to an improved method of forming metal chelate protein conjugates.

There has been a continuing interest in the art in metal chelate protein conjugates both for therapeutic and for diagnostic purposes. Representative type conjugates are disclosed, inter alia, in U.S. Pat. Nos. 4,454,106 and 4,472,509. One such type of conjugate is a metal chelate monoclonal antibody conjugate. Other proteins including, for example, polyclonal antibodies, antigens and blood proteins can also be employed in the formation of a metal chelate protein conjugate.

In general, the prior art has formed a conjugate of a chelate and protein and thereafter mixed that conjugate with the metal to be chelated. Such system is feasible as described in U.S. Pat. No. 4,472,509. In order to provide a conjugate in which substantially all the metal is contained in the chelate, however, several precautions are necessary. As a threshold matter, the protein to be used should be essentially free of metals which chelate because the presence of those metals with the protein may block the desired chelating sites. In addition, protein has an inherent ability to adventitiously bind metal along the protein molecule. Such metal may be either strongly or weakly bound depending upon the metal thereby presenting a significant challenge in removing the adventitiously bound metals from the protein. Some of the adventitiously bound metals may be (and often are) released in vivo and, particularly in the case of radioactive metals, may produce an undesirable concentration of the metal in bone marrow or the like. A process for processing metal chelate protein conjugates for the removal of adventitiously bound metals is disclosed in U.S. Pat. No. 4,472,509.

There continues to be a need for effective metal chelate protein conjugates as well as an effective method for forming a metal chelate protein conjugate that does not require substantial protein pre-purification and/or subsequent processing to remove adventitiously bound metals.

SUMMARY OF THE INVENTION

It is one object of this invention to provide a method for forming a metal chelate protein conjugate that does not require rigorous pre-purification of the protein.

It is a further object of this invention to provide a method for forming a metal chelate protein conjugate that does not result in adventitiously bound metals.

It is yet another object of this invention to provide a method for forming a radioactive metal chelate protein conjugate that does not require the use of carrier-free or no-carrier added radioactive nuclides.

It is still another object of this invention to provide an efficient method of forming a stable metal chelate protein conjugate.

It is yet a further object of this invention to provide a novel substituted diethylenetriamine as well as a novel bifunctional chelate.

It is still a further object of this invention to provide a novel metal chelate protein conjugate.

The present invention contemplates the method of forming a metal chelate protein conjugate which comprises:

contacting a metal in the absence of a protein with a bifunctional chelate having as a portion of its molecular structure a functional group attached to a carbon atom of the chelate backbone and which is stable in a dilute aqueous solution at a pH for metal chelation in the range of from about 1 to about 7 and which reacts directly with amino acid residues of a protein to form a stable covalent linkage at a conjugating pH in the range of from about 6 to about 11;

admixing said metal chelate with a protein in an aqueous solution having a pH of from about 6 to about 11 to form a stable metal chelate protein conjugate.

In another of its aspects this invention contemplates a particularly useful bifunctional metal chelate comprising a diethylenetriaminepentaacetic acid substituted on the carbon backbone with a side chain containing a nitro substituent. In still other aspects, the invention contemplates a diethylenetriaminepentaacetic acid substituted on the carbon backbone with a side chain containing an isothiocyanate substituent or an N-hydroxysuccinimide ester substituent and a metal chelate protein conjugate formed therefrom.

The practice of the method of this invention substantially eliminates adventitiously bound metal. By selection of proper functional groups on the chelate a rapid formation of the metal chelate protein conjugate is achieved. Such formation permits a variety of radioactive nuclides including those which have relatively short half lives to be effectively processed according to this invention. Moreover, since conjugates often are formed at somewhat basic pH's, a slow formation of the conjugate can result in unwanted side effects. Such side effects include hydrolysis of metals with the accompanying loss of metal from the chelate and precipitation of metal on protein surfaces as undesirable adventitiously bound metal. In addition, hydrolysis of metals can result in the formation of undesirable colloids which may be difficult to separate from the protein. Moreover, utilization of a rapid coupling reaction provides flexibility and makes a a kit practical thus expanding the types of laboratory locations at which the formation of metal chelate protein conjugates may be utilized.

A large number of reactive groups which have been indicated to be useful to couple chelates to proteins are not suitably efficient for this invention. Thus, disulfides or maleimides tend to dissociate in water at pH's that exist in vivo or in serum; nitrenes, sulfonamides, carbodiimides, sulfonyl chlorides, and anhydrides tend to be unstable in water at conjugation raction conditions; benzimidates, haloacetamides, hydrazides and diazotized amine groups tend to inefficiently conjugate; and azides and nitrenes must be coupled photolytically which can result in inefficiencies and require considerable equipment.

Yeh, *Analytical Biochemistry*, 100, 152-159 (1979) reported use of a side chain containing a COOH functional group attached to the carbon backbone of EDTA (1-(p-carboxymethoxybenzyl)-ethylenediaminetetraacetic acid). Yeh chelated both iron and indium before conjugation to protein by a carbodiimide coupling reaction. The iron and indium were employed to tie up the COOH groups of the EDTA portion of the molecule which was necessary because the coupling functional group was also a COOH group. This method requires a very large excess of bifunctional chelate and also results in some dimerization of protein. Yeh removed the iron after conjugation and then subsequently added the desirable metal ions. Yeh reported that the indium was not effective as a blocking agent for EDTA carboxylates thus resulting in an unstable metal chelate protein conjugate.

Prior art DTPA-containing protein conjugates have coupled the DTPA through a carboxylic acid group of the DTPA or through a functional group on a side chain attached to a nitrogen of the DTPA. The DTPA chelates of this invention are more stable than either or than DTPA itself.

DETAILED DESCRIPTION OF THE INVENTION

Any of the organic chelating agents (called ligands) known in the art can be employed in the practice of this invention. Such organic ligands include, inter alia, the natural or synthetic amines, porphyrins, aminocarboxylic acids, iminocarboxylic acids, ethers, thiols, phenols, glycols and alcohols or the polyamines, polyaminocarboxylic acids, polyiminocarboxylic acids, aminopolycarbocxylic acids, iminopolycarboxylic acids, nitrilocarboxylic acids, dinitrilopolycarboxylic acids, polynitrilopolycarboxylic acids, ethylenediaminetetraacetates, diethylenetriaminepenta- or tetraacetates, polyethers, polythiols, cryptands, polyetherphenolates, polyetherthiols, ethers of thioglycols or alcohols, polyaminophenols, all either acyclic, macrocyclic, cyclic, macrobicylclic or polycyclic, or other similar ligands which produce highly stable metal chelates or cryptates. One summary of chelating agents is given in U.K. patent application No. 2,109,407. Obviously, the choice of the ligand depends upon the metal to be chelated and is within the skill of the art.

According to the practice of this invention, the bifunctional chelate has as a portion of its molecular structure a functional group attached to a carbon atom of the chelate backbone and which reacts directly with amino acid residues of a protein to form a covalent linkage. Such functional groups include isothiocyanate and the N-hydroxysuccinimide ester. The functional group, in accordance with this invention, may be attached directly to the chelate backbone or may be attached to the chelate backbone through any of a wide variety of side chains. Any of a wide variety of side chains may be employed and the choice of a particular one will be within the skill of the art. The side chain may contain carbon-to-carbon, ether or thioether linkages or the like. Hydrocarbon side chains are preferred. If there are heteroatoms present, for example in ether linkages, interrupting the carbon backbone, they may be counted as carbon atoms for the purpose of chain length determinations. Such structures include, without limitation, straight or branch chain alkyl groups having 1 to about 15 carbon atoms such as methylene, ethylene, propylene, butylene, isopropylene and the like; a straight or branch chain alkene group having 2 to about 15 carbon atoms including ethene, propene, butene and the like and isomers thereof; aryl groups including phenyl, diphenyl, napthyl and the like; and alkyl aryl groups having 1 to about 15 carbon atoms in one or more branched or straight chain alkyl groups, including benzyl, phenyl ethylene, phenyl propylene and the like. The essential purpose of the side chain is only to serve as a stable link between the chelate and the functional group. The side chain should be essentially free of reactive groups other than the desired functional groups as described above. Preferred side chains include straight chain alkanes, benzyl, and phenylethylene.

Chelates having the appropriate functional groups can be prepared employing methods known in the art. Those methods include, for example, that described in *Analytical Biochemistry*, 142, 68, (1984).

In one preferred aspect, this invention provides a diethylenetriaminepentacetic acid (DTPA) having a side chain attached to the carbon backbone of the DTPA and containing a functional group which is stable in a dilute aqueous solution at a pH for metal chelation in the range of from about 1 to about 7 and which reacts directly with amino acid residues of a protein to form a stable covalent linkage at conjugating pH's in the range of from about 6 to about 11. The preferred functional groups and hydrocarbon side chains are as described above.

In order to make the substituted DTPA, a precursor compound, a diethylenetriamine, is used. The most preferred such compounds contain a nitro group attached to the carbon backbone of the diethylenetriamine. Such attachment is provided via side chains containing carbon-to-carbon, ether, thioether linkages, or the like. Depending on the DTPA chelate described, the length of the side chain and composition thereof will vary as described above. Preferred side chains linking the nitro-group to the carbon backbone are straight chain alkyl, benzyl, and phenylethylene.

In one process for producing the substituted DTPA, nitrophenylalanine is converted to the methyl ester, for example, by reacting with methyl alcohol saturated with hydrochloric acid and the methyl ester is then reacted with ethylenediamine in the presence of triethylamine in an organic solvent to form the corresponding acid amide of ethylenediamine. The compound thus formed is subsequently reduced with diborane in tetrahydrofuran and the resulting boron hydride adduct is cleaved with hydrochloric acid in ethanol to form 2-(nitrobenzyl)diethylenetriamine trihydrochloride. The diethylenetriamine can then be converted to the pentaacetic acid employing techniques well-known in the art.

In an alternate method of providing the 2-(nitrobenzyl)diethylenetriamine, nitrophenylalanine may be reacted with the amine blocking group (BOC-ON, Aldrich Chemical Co.) and the blocked amino acid is then reacted with the acetic acid salt of glycinamide in the presence of triethylamine and 1-hydroxybenzotriazole. The primary amine is then "deprotected" from BOC by refluxing with HCl in dioxane to form the corresponding peptide salt. Reduction with diborane in tetrahydrofuran followed by cleavage of the boron hydride adduct with hydrochloric acid provides 2-(nitrobenzyl)diethylenetriamine trihydrochloride. Once again, this material may be converted to the nitro-substituted pentaacetic acid by reactions well-known in the art.

The nitro-substituted pentaacetic acid is readily converted to isothiocyanate-substituted pentaacetic acid by reduction of the nitro-group to an amine group, forming the corresponding amino-substituted pentaacetic acid which is then reacted with thiophosgene. The above amino-substituted compound can be used to form two particularly useful chelates: isothiocyanate-substituted DTPA and N-hydroxysuccinimide ester-substituted DTPA. To form the first such chelate a variety of methods, well-known in the art, may be used. To form the second compound, the amine-substituted DTPA is reacted with a di-N-hydroxysuccinimide ester of a dicarboxylic acid. Suitable esters include those of the alkyl-dicarboxylic acids, or aryl-dicarboxylic acids. Preferred esters are those of malonic, succinic and glutaric acid.

Such reactions are generally performed by addition of the amine-substituted DTPA to solutions containing excess of the ester. Purification may be accomplished using reverse phase HPLC.

The 2-(nitrobenzyl)diethylenetriamine is a valuable intermediate since the nitro group can readily be converted employing reactions well-known in the art, to an amine, as well as other groups. Diethylenetriamine salts produced by many of the above techniques can, of course, be salts of acids other than hydrochloric such as hydrobromic acid, acetic acid and the like. These salts can be converted to the free amine by neutralization with, for example, triethylamine or other base and extraction into ether.

Any suitable metal can be employed in the chelate including metals which exhibit paramagnetism, metals which are fluorescent and metals which are radioactive. Representative paramagnetic metals include gadolinium and iron, fluorescent metals include several metals of the lanthanide series such as terbium and europium; and radioactive metals include radionuclides of bismuth, indium, yttrium and scandium.

Metal chelation is carried out in an aqueous solution, preferably in a dilute acid medium having a pH of about 1 to about 7 and most preferably at a pH of from about 4 to about 6. Ambient temperatures or below (to just above freezing) readily can be employed for the metal chelation. Any appropriate metal salt, either in solid form or in solution, is contacted with the chelate in solution in order to form the chelated metal. The amount of metal employed may be from tracer amounts to amounts equimolar with the chelate. A wide variety of metal salts may be employed including, for example, nitrates, iodides, chlorides, citrates, acetates and the the like. The choice of an appropriate metal salt for any given metal as well as the choice of a particularly appropriate chelate for any given metal is within the skill of the art. It will be apparent that the practice of this invention permits the processing of rather small quantities of metal and protein to form metal chelate and metal chelate protein conjugates.

The chelated metal is then mixed in aqueous solution with the desired protein at a pH of from about 6 to about 11, most preferably at a pH of from about 7 to about 9.5. Desirably, the pH is adjusted with buffered solutions such as a bicarbonate buffered solution. Once again, the choice of an appropriate buffer is within the skill of the art. The temperature of the solution can range from just above freezing to the temperature at which the chelate becomes unstable or the protein denatures. Often temperatures above 37° C. tend to denature proteins.

The choice of a protein for use in the metal chelate protein conjugate is not critical. Any desirable protein may be employed to form the conjugate. Monoclonal antibodies, of course, are often chosen as the protein for the formation of metal chelate protein conjugate both for diagnostic and for therapeutic purposes. Other suitable proteins include polyclonal antibodies, antigens and blood proteins generally. Generally, chelate and protein are mixed in a molar ratio of greater than 1:1 and generally less than about 10:1. Ratios of about 2:1 to about 4:1 are often preferred.

When either an N-hydroxysuccinimide ester or an isothiocyanate is employed in the practice of this invention, no catalyst is necessary in order to form the conjugate and pH's of from about 6 to about 9.5 are desirable. The presence of a catalyst, while not necessary, may speed the conjugation reaction by a factor of 3 or 4 or more. Suitable catalysts are general base catalysts and include triethylamine, N,N-dimethylaminopyridine, and the like.

The metal chelate protein conjugate of this invention may be used as such with appropriate pH adjustment, if needed. Alternatively, if it is desired to purify the conjugate from unconjugated chelate or products of any side reactions, the product may be purified. A variety of purification techniques known in the art may be used including column chromatography such as that described in U.S. Pat. No. 4,472,509. High-pressure liquid chromatography (HPLC) can also be used.

The invention contemplates as in vivo therapeutic procedure in which radiometal chelate conjugated monoclonal antibodies are introduced into the body and allowed to to concentrate in the target region. There are a wide variety of radiometal isotopes which form stable DTPA complexes and emit cytotoxic beta particles, Auger electrons and alpha particles. Useful beta particle emitting isotopes include Sc-46, Sc-47, Sc-48, Ga-72 and Ga-73. Bi-212 is a useful alpha emitter. The therapeutic effect occurs when the conjugates are near or in contact with and bind to the targeted cells. Cell death, it is believed, is a direct or indirect result of the radiation event of the radiometal which is positioned in close proximity to the cell.

The benefits of this aspect of the invention are several. First, the high specificity of the conjugated monoclonal antibody minimizes the total radiation dosage. Only enough radiation for the target cells need be employed. In addition, radiometal chelates generally are cleared rapidly from the body should the conjugated antibody be disrupted. The isotope can be short-lived and the affinity constant by which the isotope is retained in the DTPA chelate is very high resulting in a stably bound metal. Finally, since the amount of radiometal employed is minimized, the radiation hazard to persons preparing the administering the radiometal chelate conjugated antibody is significantly reduced.

Because of the properties of the DTPA radiometal chelate conjugated monoclonal antibody employed by the present invention, tissue damage or whole body dose during therapy are markedly reduced as compared to that from presently employed methods of radiation therapy such as isotope implants, external radiation therapy, and immunoradiotherapy employing iodine-131 labeled polyclonal or autologus antibodies. Additionally, both biological and physical half-lives of the targeting radiobiological may now be controlled, minimizing whole body radiation effects. Since radiation is targeted specifically to cell types (e.g., neoplastic cells) a therapeutic dose is delivered specifically to malignant cells, either localized or metastasized. The ability of radiometal chelate conjugatged monoclonal antibody to provide an effective dose of therapeutic radiation specifically to metastasized cells is also unique and singularly useful for cancer therapy.

In another embodiment, the present invention contemplates an in vivo diagnostic procedure which comprises introducing a metal chelate conjugated monoclonal antibody into the body, allowing sufficient time for the conjugate to localize and identifying the degree and location of localization, if any. The present invention also contemplates in vivo analytical procedures employing a chelate conjugated monoclonal antibody. The conjugated antibody of the present invention is substantially free of adventitiously or weakly chelated metal. The chelate conjugated to the antibody in the present invention is a derivative of diethylenetriaminepentaacetic acid (DTPA).

Other diagnostic and therapeutic techniques are described in U.S. Pat. No. 4,454,106, which is incorporated here by reference.

The following examples are to be used for illustrative purposes only are and not to be limited by the scope of this invention.

EXAMPLE 1

Preparation of 1-(p-isothiocyanatobenzyl)ethylene diaminetetracetic acid.

Synthesis of methyl p-nitrophenylalanine hydrochloride 1: Dry methanol (200 ml) was saturated with HCl by bubbling in a three-necked round bottom flask and cooled to $-10°$ C. p-Nitrophenylalanine (10.0 g, 47.6 mmol) was added in one portion and left to stir for two hours, then resaturated with HCl. The reaction flask was stoppered with a drying tube and left to stir at room temperature for 18 hours. The solution was evaporated to near dryness on a rotary evaporator and the precipitated product collected in a Buchner funnel. After drying under vacuum at 50° C., the yield of 1 was 10.97 grams (88.3%). A TLC of the free amino ester run in $CHCl_3$:MeOH (4:1) revealed an $R_f=0.85$-0.88. $^1H$ NMR (220 MHz, $D_2O$, pH 1.5) δ 8.20 (d, 2, J=10.0), 7.53 (d, 2, J=10.0), 4.55 (t, 1, J=11.0), 3.84 (s, 3), 3.43 (m, 2); CI-MS 225 ((M+1)/z).

Synthesis of p-nitrophenylalanine amide 2: A slurry of 1 (10.97 g, 42.1 mmol) in dry methanol (5 ml) was treated with triethylamine (6.45 ml). After clearing, anhydrous ether (200 ml) was added to the solution and cooled to $-10°$ C. for one hour. Precipitated triethylamine hydrochloride was removed by filtration and the filtrate concentrated to a limpid yellow oil. The oil was added to dry methanol (250 ml) previously saturated with $NH_3(g)$ at $-10°$ C., tightly stoppered and left at $-10°$ C. for 42 hours. The precipitated product was collected and dried under vacuum. The liquid filtrate was spotted on a TLC plate and developed with $CHCl_3$:MeOH (4:1) which revealed one spot at $R_f=0.50$, identical to that of the collected precipitate. The filtrate was therefore stripped to dryness and the remaining solid 2 combined with the precipitate (8.12 g, 92.3%): mp 160°-162° C.; $^1H$ NMR (220 MHz, DMSO-$d_6$), δ 8.07 (d, 2, J32 8.0), 7.5 (d, 2, J=8.0), 7.41 (s, 1), 7.00 (s, 1), 3.50 (t, 1, J=6.0), 3.09 (dd, 1, J=6.0, 16.0); 2.81 (dd, 1, J=6.0, 16.0) CI-MS 210 ((M+1)/z).

Synthesis of 1-(p-nitrobenzyl)ethylenediamine dihydrochloride 3: A one liter three-neck round bottom flask was fitted with a reflux condenser, septum, argon inlet and bubbler exit, then flame dried. 2 (8.12 g, 38.9 mmol) was washed into the reaction flask with dry THF (150 ml) and cooled to $-10°$ C. Next, 1M $BH_3$.THF solution (200 ml) was added with a syringe. The reaction solution was stirred one hour at $-10°$ C., then raised to a gentle reflux for 18 hours, after which it was cooled to $-10°$ C. and dry methanol (25 ml) was injected. The reaction was allowed to warm to room temperature before stripping the solvent to near dryness. Methanol (25 ml) again was added and evaporated to near dryness. The residue was taken up in dry ethanol (100 ml), saturated with HCl(g) and heated to reflux for two hours. The reaction was then tightly stoppered and left at 0° C. for 18 hours. The precipitated product 3 (8.86 g, 85.1%) was collected and dried under vacuum. $^1H$ NMR (500 MHz, $D_2O$, pH 1.0) δ 8.234 (d, 2, J=8.0), 7.634 (d, 2, J=8.0), 4.125 (m, 1), 3.543 (dd, 1, J=6.5, 18.0), 3.467 (dd, 1, J=6.5, 18.0), 3.391 (dd, 1, J=7.0, 14.0) 3,260 (dd, 1, J=7.0, 14.0); (500 MHz, $D_2O$, pH 11.5) and 8.046 (d, 2, J=8.5), 7.423 (d, 2, J=8.5), 3.061 (m, 1), 2.926 (dd, 1, J=10.0, 13.5) 2.730 (dd, 1, J=10.0, 13.5), 2.665 (dd, 1, J=16.0, 13.5), 2.592 (dd, 1, J=16.0, 13.5); CI-MS 196 ((M+1)/z).

Synthesis of 1-(p-nitrobenzyl)ethylenediaminetetraacetic acid 4: A 50 ml three-neck round bottom flask was fitted with the addition tube from an autoburette, a glass electrode, a stirring bar and a stopper. The reaction flask was charged with 3 (2.0 g, 7.465 mmol) in $H_2O$ (6 ml) and heated in a temperature controlled oil bath at 45° C. Bromoacetic acid (4.198 g, 30.2 mmol) was added in four equal portions over 4 hours while the reaction mixture was maintained at pH 10.8 by the controlled dropwise addition of 7M KOH. After the final addition, the reaction was allowed to continue for 18 hours before filtration through a medium glass frit, acidification with concentrated HBr to pH 1.8, and evaporated to dryness. A substantial amount of salt was removed by triturating with hot 100% formic acid followed by filtration on a medium frit. The filtrate was evaporated and the residue taken up in 1M formic acid and loaded onto an ion exchange column made up of a 2.6×30 cm bed of AG1×8, 200-400 mesh, anion exchange resin, formate form (Bio-Rad Corp.). The column was jacketed and maintained at 40° C. by a water bath. The product was eluted from the column with a 1M to 7M gradient of formic acid at a flow rate of 2 ml/min., monitoring at 370 nm, with a 6.5 ml fraction size. Fractions 155-206 which contained precipitated product 4 were collected by filtration and the eluant in fractions 135-237 was combined with the filtrate and stripped to dryness (2.234 g, 70.0%).

TLC of the product was performed in 1-butanol:$H_2O$ acetic acid (4:1:1) with an $R_f=0.20$ and in Methanol:10% aqueous ammonium acetate (1:1) with an $R_f=0.80$-0.83.

$^1H$ NMR (500 MHz, $D_2O$, pH 4.5) δ 8.176 (d, 2, J=8.0), 7.577 (d, 2, J=8.0), 3.928 (d, 2, J=17.0), 3,839 (q, r, J=17.0), 3,685 (d, 2, J=17.0), 3,581 (t, 1, J=12.0) 3,388 (m, 2), 3,006 (t, 1, J=10.0); (500 MHz, $D_2O$, pH 11.5) δ 8.098 (d, 2, J=7.5), 7.398 (d, 2, J=7.5, 3,40-3.00 (m, 7), 2.888 (t, 1, J=10.5), 2.720 (d, 2, J=16.0), 2,562 (t, 1, J=13.0), 2,462 (t, 1, J=12.0), 2,152 (d, 1, J=14.0); EI-MS—sample was prepared by reacting with excess bis(trimethylsilyl)trifluoroacetamide in acetonitrile; m/z (M+) 715, 700, 598, 579, 425, 920.

Synthesis of 1-(p-aminobenzyl)ethylenediaminetetraacetic acid 5: A water-jacketed three-necked flask (50 ml) was charged with 10% Pd/C (43 mg), $H_2O$ (5 ml) and a stirring bar. The center neck was attached to an atmospheric hydrogenation apparatus, one side neck was fitted with an injection valve, and the remaining neck firmly stoppered. The assembled hydrogenation apparatus was evacuated and flushed with hydrogen while the reaction flask was cooled to 4° C. 4 (427 mg, 1 mmol) was dissolved in $H_2O$ (10 ml) and 5M NaOH was added to bring the pH to 10.0. The solution was injected into the reaction flask and hydrogen uptake monitored. After 67.5 ml of gas had been consumed, the flask was disconnected from the system and the contents filtered through a fine frit coated with celite 535. The filtrate was acidified to pH 2.0, stripped to near dryness and the residual solution loaded onto an ion exchange column, 2,6×30 cm, charged with AG50W×8, 200-400 mesh, H+ form, and eluted with 0.5M ammonia. The fractions containing product, as determined by TLC, were evaporated to a solid and dried under vacuum for 18 hours (390 mg, 98.0%). The TLC of the product had an $R_f=0.10$ in 1-butanol:H$_2$O:acetic acid (4:1:1).

$^1$H NMR (500 MHz, D$_2$O, pH 1.5) δ 7.468 (m, 4), 4.109 (d, 2, J=16.0), 4.020 (d, 2, J=16.0), 3,768 (d, 2, J=17.5), 3,640 (d, 2, J=15.0), 3.887 (m, 2), 3,193 (d, 1, J=13.0), 2,798 (d, 1, J13.0), one proton obscured by doublet at 3.640; (500 MHz, D$_2$O, pH 6.0) δ 7.173 (d, 2, J=7.0), 6.959 (d, 2, J=7.0), 3.832 (d, 2, J=16.5), 3,699 (d, 2, J=16.5), 3,624 (d, 2, J=16.5) 3.568 (d, 2, J=16.5), 3,346 (t, 1, J=9.5), 3,233 (d, 1, J=14.0), 3,131 (d, 1, J=9.5), 2,679 (t, 1, J=13.0) one proton obscured by doublet at 3.624; (500 MHz, D$_2$O, pH 11.5) δ 7.033 (d, 2, J=7.0), 6.805 (d, 2, J=7.0), 3.40–3.00 (m, 4), 3,0069 (d, 2, J=16.5), 2,841 (d, 1, J=13.0) 2.725 (t, 1, J=12.0), 2.659 (d, 2, J=16.5), 2,429 (t, 1, J=12.0), 2,171 (d, 1, J=13.0), 2.096 (t, 1, J=12.0); EI-MS sample was prepared by reacting with excess bis(trimethylsilyl)trifluoroacetamide in acetonitrile; for the free amine, m/z (M+) 685, 670, 579, 396; for the silated amine, m/z (M+-15) 742 468).

Synthesis of 1-(p-isothiocyanatobenzyl)ethylenediaminetetraacetic acid 6: The precursor 5 (0.33 mmol) was taken up in H$_2$O (10 ml) and stirred rapidly in a 10 ml round bottom flask fitted with an addition funnel. The pH was adjusted to 8.5 with solid NaHCO$_3$ and thiophosgene (42 mg, 0.365 mmol) in CHCl$_3$ (10 ml) was added dropwise. Stirring was continued until the solution tested negative for amine by the fluorescamine method. The aqueous layer was taken to dryness. Purification was done by column chromatography on a 1×30 cm Florisil ™ column eluted with acetonitrile:water (30:8). The product eluted from the column cleanly as determined by TLC and was stored in a dessicator in a freezer and re-purified immediately prior to use.

The $R_f$ of the product, determined by TLC, was 0.45 in acetonitrile:water (30:8) and 0.60 in ethanol:water:acetic acid (70:25:5). The IR spectra showed an absorption at 2100 cm$^{-1}$ in Nujol ™. $^1$H NMR (500 MHz, D$_2$O, pH 5.3) δ 7.273 (q, 4, J=8.5), 3.471 (d, 1, J=17.0), 3.313 (broad singlet, 2), 3.118 (d, 1, J=14.0), 3.05–2.70 (m, 6), 2.547 (t, 1, J=13.5), 2.447 (t, 1, J=13.0), 2,257 (d, 1, J=14.0).

EXAMPLE 2

Preparation of 1-(p-isothiocyanatobenzyl)diethylenetriaminepentaacetic acid.

Synthesis of N-(2-aminoethyl)p-nitrophenylalanine amide 7: In a manner identical to the preparation of 2, 1 (4.4 g, 17.9 mmol) was treated with triethylamine (2.78 ml, 20.0 mmol) to generate the free amino ester. After removal of the solvents, the ester was taken up in methanol (5 ml) and added dropwise to ethylenediamine (35 ml) at room temperature with vigorous stirring. While TLC revealed that the reaction was essentially completed in less than one hour, the reaction was allowed to stir for 18 hours. The reaction flask was fitted with a vacuum take-off adaptor and attached to a vacuum pump with a liquid nitrogen trap in line. Removal of the solvent left a brownish solid which was dried at 50° C. under vacuum for 6 hours, and 24 hours at room temperature (4.42 g, 87.5%). TLC of the product showed an $R_f=0.10$–0.12 in chloroform:methanol (4:1).

$^1$H NMR (220 MHz, D$_2$O, pH 1.0) δ 8.23 (d, 2, J=8.0), 7.54 (d, 2, J=8.0), 4.36 (t, 1, J=7.0), 3.62 (m, 1), 3.41 (m, 3), 3.12 (m, 2); CI-MS 253 (M+I)/z).

Synthesis of p-nitrobenzyldiethylenetriamine-trihydrochloride 8: 7 (5.38 g, 21.3 mmol) was reduced with 1M BH$_3$.THF (125 ml) in a manner identical to that employed in the preparation of 3 (6.05 g, 82.3%).

$^1$H NMR (500 MHz, D$_2$O, pH 11.5) δ 8.285 (d, 2, J=9.0), 7.605 (d, 2, J=9.0), 4.118 (m, 1), 3.68–3.57 (m, 2), 3,538 (t, 2, J=7.0), 3,458 (t, 2, J=7.0), 3,378 (dd, 1, J=9, 12.5) 3,213 (dd, 1, J=9, 12.5); CI-MS 239 ((M+1)/z).

Synthesis of BOC-p-nitrophenylalanine 12 (Alternative synthetic pathway to 8 for verification purposes): p-Nitrophenylalanine (7.94 g, 37.8 mmol) was dissolved in 50% aqueous dioxane solution (60 ml) and triethylamine (0.9 ml, 56.7 mmol) added. BOC-ON (10.24 g, 41.6 mmol) (Aldrich Chemical Co.) was added and the solution stirred for two hours. Ethyl acetate (100 ml) and H$_2$O (50 ml) were next added and the contents poured into a separatory funnel. The aqueous layer was retained and extracted twice with ethyl acetate (100 ml). The aqueous layer was cooled to 0° C. and the pH was adjusted to 2.0 with 3N HCl, whereupon a precipitate formed which was collected and dried under vacuum. The filtrate was extracted with ethyl acetate twice (100 ml), dried (MgSO$_4$) and stripped to dryness. The two fractions provided to be identical and were combined (11.0 g, 94.0%). The melting point of the compound was 165° C.

$^1$H NMR (220 MHz, DMSO-d$_6$) δ 8.036 (d, 2, J=8.0), 7.29 (d, 2, J=8.0), 5.38 (d, 1, J=8.0), 4.44 (m, 1), 3.25 (dd, 1, J=6, 13.0), 3.05 (dd, 1, J=6, 13.0), 1.39 (s, 9); CI-MS 311 ((M+1)/z).

Synthesis of 1-(p-nitrobenzyl)diethylenetriamine trihydrochloride 8: Glycineamide, acetate salt (432 mg, 3.23 mmol) was dissolved in ethyl acetate (50 ml) and cooled to 0° C. Triethylamine (326 mg, 3.23 mmol) 12 (1.0 g, 3.23 mmol) and 1-hydroxybenzotriazole (383 mg, 2.84 mmol) were added in succession. Dicyclohexylcarbodiimide (731 mg, 3.55 mmol) in ethyl acetate (5 ml) was then added. The flask was stoppered with a drying tube, allowed to come to room temperature, and stirred for 48 hours. Three drops of acetic acid were then added and, after 10 minutes, the reaction mixture was filtered. The filtrate was retained and washed three times with 0.5N HCl (50 ml), then with saturated NaCl (50 ml), three times with 5% NaHCO$_3$ (50 ml) and again with saturated NaCl (50 ml). The wet organic phase was dried (MgSO$_4$) and evaporated to a solid which was dried under vacuum for 18 hours; CI-MS 367 ((M+1)/z). The product 13 (765 mg, 2.09 mmol) was deprotected by stirring for 4 hours in dioxane (40 ml) to which was added 3N HCl (65 ml). The solution was evaporated to dryness, taken up in methanol (25 ml) and again evaporated to a solid which was dried under vacuum for 18 hours; CI-MS 267 ((M+1)/z) to form 14 (1.0 g, 3.7 mmol) which was reduced by 1M BH$_3$.THF (15 ml) in a manner identical to the preparation of 3. The isolated solid (897 mg, 3.077 mmol) was identical in all respects to that from the reduction of 7.

Synthesis of 1-(p-nitrobenzyl)diethylenetriaminepentaacetic acid 9, the corresponding amine 10, the corresponding thiocyanate 11: These compounds were synthesized by methods analogous to those for compounds 4, 5 and 6 and similarly characterized by nmr and mass spectroscopy.

EXAMPLE 3

An aqueous solution of 5 millicuries of $^{111}$InCl$_3$ in 0.1 ml of 0.2 molar HCl was neutralized to pH 4.5 with a 3.0 molar solution of sodium acetate. To this was added the isothiocyanate chelate of Example 1 in an amount equal to 3 times the molar equivalent of the protein to be labeled. This procedure quantitatively complexed the indium as demonstrated by silica gel plate chromatography with elution in 50:50 solution of methanol:10% aqueous ammonium acetate.

EXAMPLE 4

The procedure of Example 3 was repeated with the isothiocyanate chelate of Example 2. Quantitative complexation was again demonstrated.

I claim:

1. A substituted diethylenetriaminepentacetic acid (DTPA) having a side chain selected from the group consisting of alkyl group having straight or branched chain of 1 to 15 carbon atoms, straight or branched chain alkene group having 2 to 15 carbon atoms and alkyl aryl group having in the alkyl portion 1 to 15 carbon atoms in one or more branched or straight chains, attached to the carbon backbone of the DTPA and containing a functional group which is stable in a dilute aqueous solution at a pH for metal chelation in the range of from about 1 to about 7 and which reacts directly with amino acid residues of a protein to form a stable covalent linkage at conjugating pH's in the range of from about 6 to about 11, said functional group being either isothiocyanate or an N-hydroxysuccinimide ester.

2. The substituted DTPA chelating agent of claim 1 being 1-(p-isothiocyanatobenzyl)diethylenetriaminepentaacetic acid.

* * * * *